United States Patent [19]

Brandman et al.

[11] 4,214,002

[45] Jul. 22, 1980

[54] PRESERVATION OF AQUEOUS SYSTEMS WITH 2-CHLORO-3-OXOBUTYRAMIDE DERIVATIVES

[75] Inventors: Harold A. Brandman, Glen Ridge; Milton Manowitz, Wayne; David L. Coffen, Glen Ridge, all of N.J.

[73] Assignees: Givaudan Corporation, Clifton; Hoffmann-La Roche Inc., Nutley, both of N.J.

[21] Appl. No.: 934,309

[22] Filed: Aug. 17, 1978

[51] Int. Cl.$^2$ .................. A01N 9/12; A01N 9/20; C07C 97/16; C07C 103/10
[52] U.S. Cl. .................. 424/300; 260/561 HL; 260/561 K; 260/561 N; 424/320; 260/161
[58] Field of Search .................. 424/300, 320; 260/561 K, 561 N, 561 HL; 560/161

[56] References Cited

U.S. PATENT DOCUMENTS

| | | | |
|---|---|---|---|
| 2,434,507 | 1/1948 | Mostek | 260/561 K |
| 2,581,842 | 1/1952 | Drake et al. | 424/320 |
| 2,587,957 | 3/1952 | Bauer et al. | 424/320 |
| 3,917,694 | 11/1975 | Reinink | 260/561 HL |

FOREIGN PATENT DOCUMENTS 828694  2/1960  United Kingdom ............... 260/561 K

OTHER PUBLICATIONS

Chem. Abst. 82, 124810(b)(1975)–Shell Inter. Res. Maatschappij.

*Primary Examiner*—Douglas W. Robinson
*Attorney, Agent, or Firm*—Robert F. Tavares; Thomas Cifelli, Jr.

[57] ABSTRACT

There is disclosed methods and compositions for inhibiting or preventing the growth of microorganisms in aqueous systems wherein the growth is inhibited or prevented by the presence of an effective amount of a 2-chloro-3-oxobutyramide derivative.

22 Claims, No Drawings

PRESERVATION OF AQUEOUS SYSTEMS WITH 2-CHLORO-3-OXOBUTYRAMIDE DERIVATIVES

THE INVENTION

A number of aqueous systems are susceptible to antimicrobial growth. Among these are cosmetics latex paints, polymer emulsions, industrial oil in water emulsions, adhesives, water used in industrial cooling towers, white water in the paper mills and the like. The growth of bacteria and fungi in such systems can be a serious problem if not properly controlled. For example, industrial aqueous systems are susceptible to slime formation which, if unchecked, can cause severe maintainance and production problems. Similarly, consumer products such as cosmetics can be damaged by the growth of bacteria, fungi or algae.

There is, consequently, a continuing effort to provide effective and economical antimicrobial agents which protect these systems. The finding of this invention is that compositions and methods utilizing 2-chloro-3-oxobutyramide derivatives provide effective control of such antimicrobial growth. The compounds of this invention have been found effective against a broad spectrum of microorganisms including gram positive bacteria, gram negative bacteria and molds. The breadth of such activities is illustrated in the examples.

The 2-chloro-3-oxobutyramide derivatives of this invention can be represented by the formula:

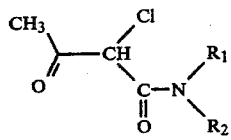

wherein $R_1$ is hydrogen or methyl and $R_2$ is selected from the group consisting of hydrogen, methyl, alkanoyl or carboalkoxy.

Two of these compounds have been reported in the chemical literature. The 2-chloro-3-oxobutyramide is reported in Chemical Abstracts 42:p2615a and the 2-chloro-N,N-dimethyl-3-oxobutyramide (also known as α-chloro-N,N-dimethylacetoacetamide) is reported in Chemical Abstracts 52:2067c. Neither reference discloses or suggests the effectiveness of these compounds in preventing antimicrobial growth.

DESCRIPTION OF THE PREFERRED EMBODIMENTS

Formula I represents the compounds of this invention. While the N,N-disubstituted analogs such as 2-chloro-N,N-dimethyl-3-oxobutyramide show a high level of activity, those in which $R_1$ is hydrogen are somewhat more active and are preferred.

Those compounds of formula I wherein $R_2$ is acyl or carboalkoxy are novel. Of these, the lower analogs wherein $R_2$ is acetyl, propionyl, butyroyl, carbomethoxy, carbethoxy, carbopropoxy and carbobutoxy are preferred. Especially preferred are N-acetyl-2-chloro-3-oxobutyramide, N-carbomethyoxy-2-chloro-3-oxobutyramide and N-carbethoxy-2-chloro-3-oxobutyramide.

The compounds of this invention may be added to the aqueous systems or formulations undiluted or dissolved in organic solvents such as alcohols, acetone, dimethylformamide and the like. They may be added alone or in combination with other biocides and/or functional compounds such as antioxidants, anticorrosive agents, surfactants, etc.

Concentrations from about 0.005% to above 0.3% are effective. Use of larger concentrations, while feasible, is recommended only for unusual applications. It is preferred to use concentrations from about 0.05% to about 0.15%.

The compounds of this invention can be used as preservatives for oil in water emulsions. A number of oil water emulsions are used in industry, for example in the high speed metal working and textile industries, for their cooling, lubricating, antistatic and anticorrosive properties. Unless adequately protected by an effective preservative, such systems are susceptible to bacterial decomposition producing obnoxious odors and potential health hazards. [Detailed descriptions of these systems, their microbiological problems and difficulties in their preservation can be found in Bennet, E. O., Soap Chem. Specialties, 32, 46 (1956) and Fabian, F. W. & Pivnick, H., Applied Microbiology, 1, (1953).]

In practicing the invention, the compounds may be added by directly dissolving them in the concentrated oil and then mixing with water to form the water oil emulsion, or they may be added to the final emulsion either undiluted or dissolved in a solvent such as dimethylformamide, alcohol, acetone, etc. Similar methods known in the art for adding preservatives to water and oil emulsions may also be used.

There can be used as little as about 0.005%. Although amounts greater then 0.3% are operable, they are recommended only for unusual applications. It is preferred to use amounts in the range of from about 0.01% to about 0.2%, with amounts in the range of about 0.02% to 0.10% being especially preferred.

The 2-chloro-3-oxobutyramide derivatives are also effective as cosmetic preservatives [Problems encountered in the preservation of cosmetics are described by Dunnigan, A. P., Drug and Cosmetic Industries, 103, 43, (1968)].

The compounds may be added to the finished cosmetic product directly or dissolved in suitable solvents such as alcohol, acetone, dimethyl formamide and the like. Alternatively the compounds may be dissolved in the oils or other raw materials used in the formula and then formulated in the final product.

In cosmetic preparations, concentrations as low as 0.01% are found to be operable. Concentrations greater than 0.30%, while operable, are recommended only for unusual applications. Concentrations in the range of from about 0.02% to about 0.2% are preferred with concentrations of about 0.05% to 0.10% being especially preferred.

The 2-chloro-3-oxobutyramides derivatives are effective as slimicides. For example it can be used to protect so-called white water systems utilized in paper manufacture from the formation of slimes and the like which are known to affect these systems. Concentrations as low as 0.005% are found to be operable. Concentrations greater than 0.20%, while operable, are recommended only for unusual applications. Concentrations in the range of from about 0.007% to about 0.15% are preferred with concentrations of about 0.01% to about 0.10% being especially preferred.

While the compounds are effective when added directly, it is preferred to add them dissolved in a suitable solvent such as diethylene glycol, dipropylene glycol or polyethylene glycol and the like. Other methods known in the art for adding preservatives to such aqueous systems may also be used.

ILLUSTRATION OF PREFERRED EMBODIMENTS

A number of examples are provided herein to illustrate the preferred embodiments of this invention. The examples provided are included for the sole purpose of illustrating the preferred embodiments and should not be construed as limiting. They are intended to embrace any equivalents or obvious extensions which are known or should be known to a person skilled in the art.

EXAMPLE I

General Antimicrobial Activity

General antibacterial and antifungal activity was evaluated by a 5-fold serial dilution test in agar. In this test, compounds were prepared as 6% solutions in dimethylformamide or ethanol. The 6% solution was then 5-fold serially diluted in test tubes to give the desired concentrations when mixed with agar and poured into sterile Petri dishes. Tryptone glucose extract agar was used for the bacterial testing; mildew glucose agar for the fungal testing. The bacterial plates were spot inoculated with 24-hour nutrient broth cultures and incubated at 37° C. for 48 hours. The fungal plates were spot inoculated with spore suspensions and incubated at 28° C. for seven days. At the end of the incubation periods, all plates were examined for growth. The minimum inhibitory concentration (MIC) for each organism is expressed in Table I. In the ranges preferred, growth is observed only at the lower concentration.

The activity is presented in Tabular Form (Table I) using the following key.

| Bacteria | Fungi |
|---|---|
| $B_1$ Staphylococcus aureus | $F_1$ Aspergillus niger |
| $B_2$ Escherichia coli | $F_2$ Aspergillus oryzae |
| $B_3$ Psuedomonas aeruginosa | $F_3$ Penicillium piscarium |
| $B_4$ Proteus vulgaris | $F_4$ Aureobasidium pullulans |
| $B_5$ Bacillus subtilis | |

| ACTIVITY RANGE | |
|---|---|
| 0 = >1920 mcg/ml | 5 = 0.6–3.1 mcg/ml. |
| 1 = 384–1920 mcg/ml. | 6 = 0.12–0.6 mcg/ml. |
| 2 = 76.8–384 mcg/ml. | 7 = 0.03–0.12 mcg/ml. |
| 3 = 15.3–76.8 mcg/ml. | 8 = <0.30 mcg/ml. |
| 4 = 3.1–15.3 mcg/ml. | |

*In the ranges presented, growth is observed only in the lower concentrations.

TABLE I $$\underset{O}{\overset{Cl}{\underset{\diagdown}{\diagup}}} \hspace{-2mm} \underset{CON{\diagdown}R_2}{\overset{H}{\diagdown}R_1}$$

Minimum Inhibitory Concentration Range

| $R_1$ | $R_2$ | BACTERIA | | | | | FUNGI | | | |
|---|---|---|---|---|---|---|---|---|---|---|
| | | $B_1$ | $B_2$ | $B_3$ | $B_4$ | $B_5$ | $F_1$ | $F_2$ | $F_3$ | $F_4$ |
| H | H | 3 | 3 | 3 | 3 | 3 | 3 | 3 | 3 | 3 |
| H | $COCH_3$ | 2 | 3 | 3 | 2 | 2 | 2 | 2 | 2 | 2 |
| H | $COOC_2H_5$ | 2 | 2 | 2 | 2 | 2 | 2 | 2 | 2 | 2 |
| $CH_3$ | $CH_3$ | 1 | 2 | 1 | 2 | 1 | 1 | 1 | 1 | 2 |

EXAMPLE II

Utility as a Cosmetic Preservative

The 2-Chloro-3-oxobutyramide derivatives are effective cosmetic preservatives. Two-fold serial dilutions of 6% solutions of the 2-haloacetoacetic acid derivatives in dimethylformamide were added to a cosmetic lotion of the following formulation:

| | |
|---|---|
| Stearic acid | 1.4 g |
| Arlacel 60 (sorbitan monostearate) | 0.7 g |
| Tween 20 Polyoxethylene (20) sorbitan monostearate | 1.6 g |
| Distilled water | 94.0 g |

The lotions were inoculated with both Pseudomonas aeruginosa and Aspergillus niger and incubated at 28° C. At weekly intervals, the lotions were examined for microorganisms by conventional streak-plate methods or by macroscopic observation. The lotions were then reinoculated with the test organisms and reincubated. Table II shows the minimum inhibitory concentration that was effective in preventing microbial growth for the four week period.

TABLE II $$\underset{O}{\overset{Cl}{\underset{\diagdown}{\diagup}}} \hspace{-2mm} \underset{CON{\diagdown}R_2}{\overset{H}{\diagdown}R_1}$$

| Compound | | Pseudomonas aeruginosa Week | | | | Aspergillus niger Week | | | |
|---|---|---|---|---|---|---|---|---|---|
| $R_1$ | $R_2$ | 1 | 2 | 3 | 4 | 1 | 2 | 3 | 4 |
| H | H | 5 | 5 | 4 | 4 | 5 | 5 | 4 | 2 |
| H | $COCH_3$ | 5 | 5 | 4 | 4 | 5 | 4 | 3 | 2 |
| H | $COOC_2H_5$ | 5 | 4 | 4 | 4 | 4 | 3 | 3 | 3 |
| $CH_3$ | $CH_3$ | 2 | 2 | 2 | 2 | 1 | 1 | 1 | 1 |

Key:
0 = >2000 mcg/gm
1 = 1000–2000 mcg/gm
2 = 500–1000 mcg/gm
3 = 250–500 mcg/gm
4 = 125–250 mcg/gm
5 = 63–125 mcg/gm
6 = 32–62.5 mcg/gm
7 = 16–31.3 mcg/gm
8 = 8–15.6 mcg/gm
9 = <8 mcg/gm

EXAMPLE III

The utility of the 2-chloro-3-oxobutyramide derivatives in water and oil emulsions is illustrated below using a commercially available cutting oil.

In running these tests, two-fold serial dilutions of 6% solutions of the compound in dimethylformamide was added to 3.3% cutting oil emulsions. The emulsions were prepared by diluting with water a commercially available cutting oil concentrate. The emulsions were inoculated with a culture of Pseudomonas aeruginosa and incubated at 28° C. on a rotary shaker. At weekly intervals, the emulsions were examined for bacteria by conventional streakplate methods. The emulsions were then reinoculated with Pseudomonas aeruginosa and reincubated.

TABLE III

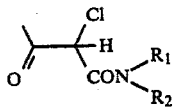

Minimum Inhibitory Concentration Range
(Micrograms/milliliter)
*Pseudomonas aeruginosa*

| Compound | | Week | | | |
|---|---|---|---|---|---|
| R₁ | R₂ | 1 | 2 | 3 | 4 |
| H | H | 6 | 3 | 3 | 3 |
| H | COCH₃ | 4 | 3 | 2 | 2 |
| H | COOC₂H₅ | 4 | 3 | 3 | 2 |
| CH₃ | CH₃ | 2 | 1 | 1 | 1 |

The highest level of the chemical inhibiting growth and the lowest level at which growth occurs indicate the activity range for that compound.

| | |
|---|---|
| 0 = >500 mcg/ml | 4 = 32–63 mcg/ml |
| 1 = 250–500 mcg/ml | 5 = 16–32 mcg/ml |
| 2 = 125–500 mcg/ml | 6 = 8–16 mcg/ml |
| 3 = 63–125 mcg/ml | 7 = 4–8 mcg/ml |
| | 8 = 2–4 mcg/ml |

EXAMPLE IV

The utility of the 2-chloro-3-oxobutyramide derivatives as a slimicide for pulp and paper mill water systems was demonstrated by the following study.

Various quantities of a 6% solution of this compound in dimethylformamide were incorporated into 24 ml of a test substrate composed as follows:

84.4 g Whatman No. 2 powered cellulose
2.6 g Sodium nitrate
1.0 g Calcium sulfate
6.5 g Maltose
1.0 g Nutrient Broth, Difco
10.0 ml Mersize Rm 70R (Monsanto)
2.5 ml 2% Alum
900 ml Distilled water The samples were inoculated with four different organisms and incubated at 28° C. At weekly intervals the samples were examined for the presence of microbial growth and reinoculated during a total incubation period of four weeks. The results are tabulated in Table IV.

TABLE IV

Effectiveness of 2-Chloro-3-oxobutyramides Derivatives as Slimicides (mcg/ml)

A. 2-Chloro-3-oxobutyramide

| Organism | Weeks* | | | |
|---|---|---|---|---|
| | 1 | 2 | 3 | 4 |
| P. aeruginosa | 62.5 | 62.5 | 62.5 | 62.5 |
| E. aerogenes | 62.5 | 62.5 | 62.5–125 | 62.5–125 |
| A. niger | 62.5 | 62.5 | 62.5 | 62.5 |
| P. piscariuim | 62.5 | 62.5–125 | 125–250 | 125–250 |

B. N-Acetyl-2-Chloro-3-oxobutyramide

| Organism | Weeks* | | | |
|---|---|---|---|---|
| | 1 | 2 | 3 | 4 |
| P. aeruginosa | 62.5 | 62.5 | 62.5 | 62.5 |
| E. aerogenes | 62.5–125 | 125–250 | 250–500 | 250–500 |
| A. niger | 62.5–125 | 62.5–125 | 62.5–125 | 62.5–125 |
| P. piscarium | 62.5 | 6.25–125 | 62.5–125 | 62.5–125 |

*Data is given in mcg/ml. In a given range growth occurs at the lower concentration and no growth occurs at the higher concentration. The lowest concentration tested was 62.5 mcg/ml and that value given above indicates that no growth was observed at the minimum concentration.

EXAMPLE V

The following illustrates methods by which the compounds used in Examples I–IV may be prepared.

2-Chloro-3-oxobutyramide (a) From α-chloro-β-aminocrotononitrile: The nitrile (5 g) was added to a solution of sulfuric acid (5 g) in water (10 ml) and the solution kept for two days. This resulted in partial hydrolysis to α-chloro-α-cyanoacetone which formed a separate layer. This was extracted into ether, the ether evaporated, and the residue taken up in conc. HCl (10 ml) and left overnight. A precipitate of ammonium chloride (900 mg) was filtered out and washed with ether, the filtrate was evaporated to a small volume and ether (50 ml) was added. This mixture was dried with Na₂SO₄, filtered, evaporated, the residue taken up in warm CH₂Cl₂, dried again and evaporated. The residue solidified on standing, it was triturated with a small volume of CH₂Cl₂, filtered and washed with CH₂Cl₂ and then dried to give 1.54 g of colorless crystals. By concentrating the filtrate to ca. 2 ml a second crop of 0.63 g was obtained (combined yield=37%).

(b) From α-chloro-α-cyanoacetone: A mixture of this material (80 g) in conc. HCl (100 ml) required cooling in ice to control the hydrolysis reaction. When the exotherm subsided, the solution was left overnight and worked up as in (a) to give 28.5 g (31%) of the amide in three crops. An alalytical sample prepared by vacuum sublimation had m.p. 78°–85°, ir (CHCl₃) 3200–3500, 1730 (shoulder), 1700, 1630, and 1575 cm⁻¹; nmr (CDCl₃) 2.11 and 2.40 (CH₃ of ketone and enol), 4.80 (CH of ketone), and 6.5 (broad, NH₂ and OH of enol); and mass spectrum m/e 43 (100%) and 135 (m+).

Anal. Calcd for C₄H₆ClNO₂: C, 35.44; H, 4.46; Cl, 26.15; N, 10.33. Found: C, 35.39; H, 4.50; Cl, 26.31; N, 10.36.

(c) From α-chloro-β-aminocrotonamide: A mixture of α-chloro-β-aminocrotonamide (4 g), and conc. HCl (4 ml), in ether (4 ml) was stirred for 1 hr. The mixture was then diluted with CH₂Cl₂ (20 ml), dried with Na₂SO₄ and decanted. The solid was thoroughly washed several times with ether and the combined organic layers evaporated. The wet residue was taken up in ether, diluted with benzene and again evaporated to give 3.8 g (94.3%) of pale yellow ketone, identified by ir, tlc and mp.

N-Acetyl-2-chloro-3-oxobutyramide

A solution of 2-chloro-3-oxobutyramide (1 g) in acetic anhydride (5 ml) containing acetyl chloride (1 ml) was heated in a 100° oil bath for 2 hours. Excess reagent was evaporated under reduced pressure and the residue was vacuum distilled in a kugelrohr apparatus. The distilled product crystallized to give a colorless solid with mp 54°–8°; ir (Nujol) 3200 and 1700 cm⁻¹ (broad); nmr (CDCl₂) 2.28 (CH₃), 2.47 (CH₃), 5.53 (CH), and 9.7 ppm (NH), (a weaker set of singlets corresponding to the enol appears at 2.23, 2.52, and 8.7 ppm); mass spectrum m/e 43 (100%), 93, 135, and 177 (M+).

Anal. Calcd for $C_6H_8ClNO_3$: C, 40.58; H, 4.54; Cl, 19.97; N, 7.89. Found: C, 40.83; H, 4.40; Cl, 20.08; N, 8.03.

N-Carboethoxy-2-chloroacetoacetamide

A mixture of diketene (25 g), urethane (20 g), and acetic acid (75 ml) was refluxed for 25 minutes. Evaporation of the acetic acid under reduced pressure gave a syrup which crystallized on scratching. Recrystallization from benzene gave 16.6 g (32.5%) of N-carbethoxyacetoacetamide as colorless needles.

The N-carbethoxyacetoacetamide (12.7 g from above reaction) was dissolved in methylene chloride (50 ml) and cooled in an ice bath. Sulfuryl chloride (10.0 g) was added dropwise to the reaction mixture. After refluxing for 45 minutes the solvent was evaporated under reduced pressure. The resulting colorless oil crystallized over night to give 15.2 g (99%) colorless product. An analytical sample recrystallized from $CHCl_3$/cyclohexane had mp 69.5°–70.0°; ir (Nujol) 3200, 1760 (broad), 1540 cm$^{-1}$; nmr (CDCl$_3$) 1.35 (t, 3H, J=7), 2.45 (s, 3H), 4.30 (q, 2H, J=7), 5.75 (s, 1H), 9.0 (s, 1H),; and mass spectrum m/e 43 (100%) and 207 (M+).

Anal. Calcd for $C_7H_{10}ClNO_4$: C, 40.50; H, 4.85; Cl, 17.08; N, 6.75. Found: C, 40.61; H, 4.61; Cl, 16.92; N, 6.71.

N,N-Dimethyl-2-chloroacetoacetamide

Diketene (42 g, 0.5 mole) was mixed with ice and water (200 ml) and treated with 25% aq. dimethylamine (90 ml). On completion of the addition, the solution was allowed to warm to room temperature and stirred for 30 min. It was then cooled with an ice bath, acidified with conc. HCl (250 ml) and treated with aq. sodium hypochlorite ("Chlorox", 800 ml) by rapid, dropwise addition. After warming to room temp., the resulting mixture was extracted three times with 400 ml portions of methylene chloride. After drying and evaporation of solvent the product was vacuum distilled to give 67.65 g (83%) of pale yellow liquid with bp 97°-8°/0.05 mm; ir film 1730 and 1645 cm$^{-1}$; nmr (CDCl$_3$) 2.40 (s, 3H), 3.03 (s, 3H), 3.20 (s, 3H), and 5.30 ppm (s, 1H); mass spectrum m/e 43 and 163 (M+).

Anal. Calcd for $C_6H_{10}ClNO_2$: C, 4405; H, 6.16, Cl, 21.67; N, 8.56. Found: C, 44.31; H, 6.29, Cl, 21.73; N, 8.66.

We claim:

1. A method of inhibiting or preventing the growth of bacteria or fungi in an aqueous composition subject to spoilage thereby which comprises incorporating in said composition a bactericidally or fungicidally effective amount of a compound of the formula:

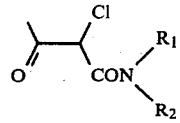

wherein $R_1$ is hydrogen or methyl and $R_2$ is hydrogen, methyl, acetyl, propionyl, butyroyl, carbomethoxy, carbethoxy, carbopropionoxy, or carbobutoxy.

2. The method of claim 1 wherein $R_1$ is hydrogen.

3. The method of claim 1 wherein the compound used is 2-chloro-3-oxobutyramide.

4. The method of claim 3 wherein the composition to be protected is a cosmetic formulation.

5. The method of claim 3 wherein the composition to be protected is a water and oil emulsion.

6. The method of claim 3 wherein the composition to be protected is a pulp and paper mill water system.

7. The method according to claim 3 wherein active compound is utilized at a level of from about 0.01% to about 0.2%.

8. The method of claim 1 wherein the compound used is N,N-dimethyl-2-chloro-3-oxobutyramide.

9. The method of claim 8 wherein the composition to be protected is a cosmetic formulation.

10. The method of claim 8 wherein the composition to be protected is a water and oil emulsion.

11. The method of claim 8 wherein the composition to be protected is a pulp and paper mill water system.

12. The method according to claim 5 wherein active compound is utilized at a level of from about 0.01% to about 0.2%.

13. The method of claim 1 wherein the compound used is N-acetyl-2-chloro-3-oxobutyramide.

14. The method of claim 13 wherein the composition to be protected is a cosmetic formulation.

15. The method of claim 13 wherein the composition to be protected is a water and oil emulsion.

16. The method of claim 13 wherein the composition to be protected is a pulp and paper mill water system.

17. The method according to claim 13 wherein active compound is utilized at a level of from about 0.01% to about 0.2%.

18. The method of claim 1 wherein the compound used is N-carbethoxy-2-chloro-3-oxobutyramide or N-carbomethoxy-2-chloro-3-oxobutyramide.

19. The method of claim 18 wherein the composition to be protected is a cosmetic formulation.

20. The method of claim 18 wherein the composition to be protected is a water and oil emulsion.

21. The method of claim 18 wherein the composition to be protected is a pulp and paper mill water system.

22. The method according to claim 18 wherein active compound is utilized at a level of from about 0.01% to about 0.2%.

* * * * *